United States Patent [19]

Bourque

[11] 4,340,676
[45] Jul. 20, 1982

[54] METHOD OF CRYSTALLIZING RIBULOSE, 1,5-BISPHOSPHATE CARBOXYLASE/OXYGENASE FROM PHOTOSYNTHETIC ORGANISMS, PARTICULARLY PLANT LEAVES

[75] Inventor: Don P. Bourque, Tucson, Ariz.

[73] Assignee: University Patents, Inc., Norwalk, Conn.

[21] Appl. No.: 190,233

[22] Filed: Sep. 24, 1980

[51] Int. Cl.$^3$ .............................................. C12N 9/88
[52] U.S. Cl. ................................... 435/232; 435/816; 435/287
[58] Field of Search ...................... 435/232; 426/655; 260/112 R

[56] References Cited

U.S. PATENT DOCUMENTS

| | | | |
|---|---|---|---|
| 2,600,903 | 6/1932 | Miller | 426/655 X |
| 3,780,183 | 12/1973 | Edwards et al. | 426/655 X |
| 3,823,128 | 7/1974 | Bickoff et al. | 426/655 X |
| 4,268,632 | 5/1981 | Wildman et al. | 435/232 |

OTHER PUBLICATIONS

Chan et al., Science vol. 176, pp. 1145–1146, (1972).
Johal et al., Science vol. 204, pp. 75–77, (Apr. 1979).
Methods in Enzymology vol. 69, pp. 326–336, (1980).

*Primary Examiner*—Lionel M. Shapiro
*Attorney, Agent, or Firm*—Mason, Kolehmainen, Rathburn & Wyss

[57] ABSTRACT

Fraction I protein from plant leaves is purified and subsequently crystallized. The crystallization methods disclosed herein unexpectedly produce crystallization in all crop leaves examined, although for some species modification by salt addition is required to achieve crystallization and to prevent formation of substantial percentages of amorphous protein precipitates. It has been found that a fraction I protein solution, when mixed with a precipitant solution having a pH generally within the range of 4.8–7.2, in an amount and at a pH sufficient to provide a mixed solution (protein solution mixed with precipitant solution) having a final pH in the range of 6.6–7.0, causes crystallization of fraction I protein from plant leaves, provided that the precipitant solution is at a pH lower than the pH of the protein solution. Optimum results have been obtained when the pH of the precipitant solution is in the range of 5.0 to 6.0 and the protein solution in the range of 7.0 to 7.5. For certain species such as potato and tobacco, the protein solution should include a salt, such as sodium chloride, capable of increasing the solubility of the protein in water, to avoid the precipitation of fraction I protein in amorphous form before conditions are proper for crystallization.

60 Claims, 1 Drawing Figure

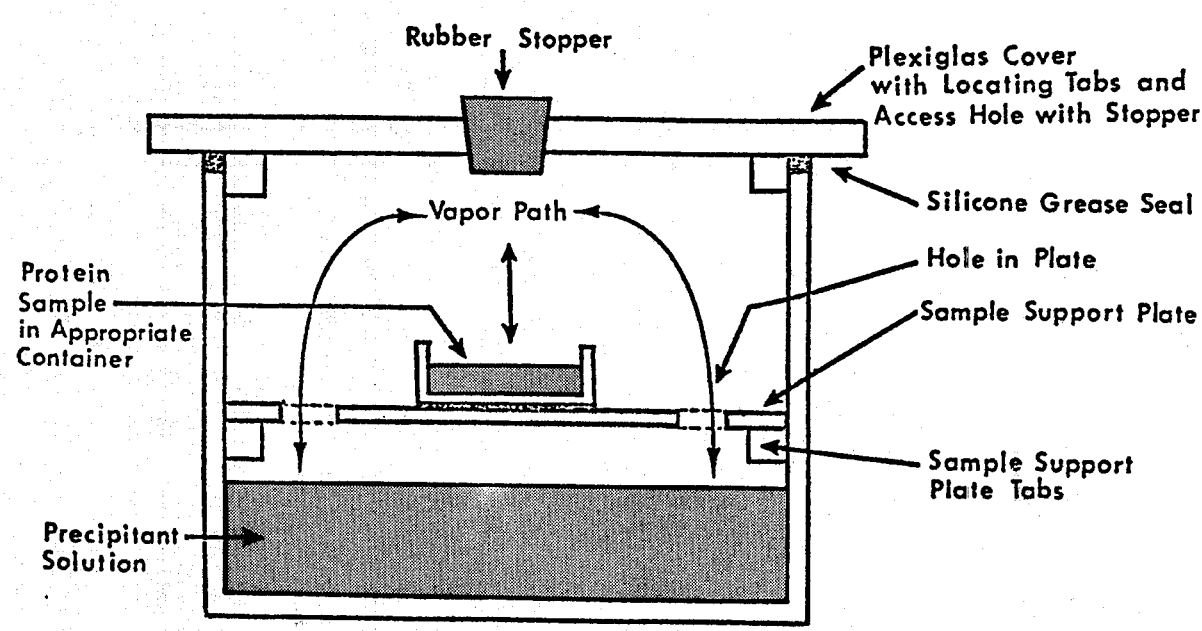

METHOD OF CRYSTALLIZING RIBULOSE, 1,5-BISPHOSPHATE CARBOXYLASE/OXYGENASE FROM PHOTOSYNTHETIC ORGANISMS, PARTICULARLY PLANT LEAVES

FIELD OF THE INVENTION

The present invention relates to a method of crystallizing protein from photosynthetic organisms. More particularly, the present invention relates to methods of crystallizing fraction I protein, ribulose-1,5-biphosphate carboxylase/oxygenase [E.C.,4.1.1.39], from green plant matter such as plant leaves.

BACKGROUND OF THE INVENTION

Interest in leaf protein concentrates for animal and human consumption has increased in recent years as a result of an anticipated world-wide need for alternate protein sources and a desire to derive maximum usefulness from agricultural crops. In order to develop alternate methods for purification of leaf proteins as potential nutritional supplements, I have found methods to purify and crystallize fraction I protein from a number of plant species, particularly crystallization of the fraction I protein of plants which are major agricultural crops and have not been previously obtained. The methods of the present invention apply to any photosynthetic organisms.

Ribulose-1,5-bisphosphate carboxylase/oxygenase [E.C.,4.1.1.39], fraction I protein, is a complex, multimeric enzyme found in a variety of photosynthetic organisms which possesses two apparently counterproductive activities. Ribulose-1,5-biphosphate carboxylase/oxygenase reacts with $CO_2$ in an initial reaction of the well known $C_3$ photosynthetic carbon reduction cycle and catalyzes a carboxylation reaction of ribulose-1,5-bisphosphate to yield two moles of 3-D-phosphoglycerate. Molecular oxygen, if present, will compete with $CO_2$ for the catalytic site, resulting in the oxygenation of ribulose-1,5-bisphosphate. The products of this initial reaction in the $C_2$ photorespiratory carbon oxidation cycle are 3-D-phosphoglycerate and 2-phosphoglycolate. Net flux of glycolate from the plant chloroplast provides the substrate for photorespiration which results in a net loss of fixed carbon as $CO_2$.

The ribulose-1,5-bisphosphate carboxylase/oxygenase holoenzyme from eukaryotic sources sediments at 18S (Svedberg constant), has a molecular weight of approximately 550,000 and is composed of eight each of large and small subunits. The large subunits, which contain the catalytically-active site, have a molecular weight of approximately 55,000 and are coded by chloroplast DNA. In contrast, the genetic information for the small subunits (15,000 molecular weight) is located in the nuclear genome. Although believed to be regulatory in nature, the precise function of the small subunits remains enigmatic.

The forces which cause ribulose-1,5-bisphosphate carboxylase/oxygenase, and other proteins, to crystallize are complex and poorly understood. Solubility properties of proteins differ widely and are a function of the protein under investigation. Therefore, to develop a successful crystallization strategy, one must identify and understand the solubility properties of the particular protein of interest. A precipitant can be used to aid in bringing about supersaturation in order to induce nucleation and crystallization of macromolecules. Particular attention has been placed on selecting an appropriate precipitant and determining the concentrations required for crystallization. Polyethylene glycol 4000, 6000 and $(NH_4)_2SO_4$ have been found to be effective precipitants, under controlled pH conditions disclosed herein, for crystallization of ribulose-1,5-biphosphate carboxylase/oxygenase from many diverse plant species. The crystallization methods described herein may vary slightly between various plant species and guidelines are provided for crystallization of fraction I proteins from leaves of alfalfa, tomato, corn, spinach, cotton, potato and tobacco to enable crystallization from essentially any photosynthetic organisms.

DESCRIPTION OF THE PRIOR ART

In my preliminary work leading to the present invention, I was able to crystallize fraction I protein from tobacco (J. T. Bahr, D. P. Bourque, H. J. Smith, J. Agric. Food Chem. 25, 783, 1977) using the standard crystallization method of Chan et al. (P. H. Chan, K. Sakano, S. Singh, S. G. Wildman, Science 176, 1145, 1972), but for unknown reasons, this standard crystallization method, examined under a wider range of pH, temperature and ionic strengths, failed to produce crystallization of fraction I protein from spinach, maize or cotton. This preliminary work confirmed the work of Chan et al. that only $MgCl_2$ and $NaHCO_3$-treated protein could be crystallized by low salt dialysis, although there are numerous similarities in the chemical and physical properties of fraction I proteins from many photosynthetic organisms.

In my later work leading to the present invention, I was able to crystallize fraction I protein from spinach and tomato using a polyethylene glycol precipitant (D. P. Bourque, Nonconventional Proteins and Foods [National Science Foundation, Research Applied to National Needs (RANN), Washington, D.C., 1977], p. 157, and S. Johal, D. P. Bourque, Science, 204, 75, 1979) either by analytical or preparative scale vapor diffusion.

The solubility properties of various plant proteins as well as concentrations of various fraction I protein precipitants (herein defined as a compound or mixture of two or more compounds capable of tying up or sequestering the solvent, i.e., water away from the protein) have been studied in an attempt to achieve an essentially saturated fraction I plant protein solution conductive to protein precipitation, and ideally to achieve crystallization, as described in my above cited RANN, Bahr et al., and Johal and Bourque articles. The study of precipitant concentration and minimum protein solubilities achieved via precipitant solutions has enabled the controlled precipitation of proteins from spinach, maize, cotton, and tomato. The tomato fraction I protein could be crystallized using the low salt dialysis method of Chan et al. Microdiffusion methods have been shown to be useful in the crystallization of fraction I protein from tobacco (T. S. Baker, D. Eisenberg, F. A. Eiserling, Science 196, 293, 1977; and T. S. Baker, W. S. Suh, and D. Eisenberg, Proc. Nat. Sci. 74, 1037, 1977).

In accordance with the present invention, new and improved methods have been found for crystallization of fraction I protein from most, if not all, plant leaves to provide a high quality pure protein from plant leaves especially suitable for use as a nutritional supplement.

SUMMARY OF THE INVENTION

In brief, the present invention involves the purification of fraction I protein from plant leaves and subsequent crystallization. The crystallization methods disclosed herein unexpectedly produce crystallization in all crop leaves examined, although for some species modification by salt addition is required to achieve crystallization and to prevent formation of substantial percentages of amorphous protein precipitates.

Fraction I proteins previously have been purified using tris-HCl purification buffers—see Chan et al., Science, 176, 1145 (1972), and Bahr, et al., J. Agric. Food Chem. 25, 783 (1977). Any method for fraction I protein separation and purification from plant leaves is useful in accordance with the present invention.

In accordance with the present invention, it has been found that a fraction I protein solution, when mixed with a precipitant solution having a pH generally within the range of 4.8–7.2 in an amount and at a pH sufficient to provide a mixed solution (protein solution mixed with precipitant solution) having a final pH in the range of 6.6–7.0, causes crystallization of fraction I protein from plant leaves provided that the precipitant solution is at a pH lower than the pH of the protein solution. To achieve the full advantage of the present invention, the precipitant solution should have a pH at least 1.0 lower than the pH of the protein solution. Optimum results have been obtained when the pH of the precipitant solution is in the range of 5.0 to 6.0 and the protein solution in the range of 7.0 to 7.5. For certain species such as potato and tobacco, the protein solution should include a salt, such as sodium chloride, capable of increasing the solubility of the protein in water, to avoid the precipitation of fraction I protein in amorphous form before conditions are proper for crystallization.

BRIEF DESCRIPTION OF THE DRAWING

The drawing shows a vapor diffusion apparatus for dehydration of the protein solution.

DETAILED DESCRIPTION OF THE INVENTION

I. Purification

Any fraction I plant protein purification process can be used to separate and purify fraction I protein from plant leaves, as well known in the art. Generally, separation and purification comprises forming a protein precipitate by washing the leaves to remove external impurities; homogenizing the leaves in a high salt (i.e., 1.0 M NaCl) buffer, for example in a blender; filtering the homogenate to remove relatively large solids; centrifuing to obtain a supernatant containing soluble protein; exchanging a low salt buffer (i.e., 0.2 M NaCl) for the high salt buffer, for example in a Sephadex column previously equilibrated with the low salt buffer; eluting the protein solution from the column with the low salt buffer; and precipitating the protein by adding a precipitant, such as ammonium sulfate, in an amount to provide 30% to 50% precipitant saturation. The protein precipitate at this stage can be crystallized, as described hereinafter.

Alternatively, the fraction I protein precipitate can be further purified as follows: the precipitate is re-dissolved in a minimum amount of low salt buffer and a low salt buffer exchanged for the precipitant, such as by dialysis against the low salt buffer; and the protein solution then applied to the top of a sucrose gradient, i.e., 5–35% by weight sucrose in low salt buffer and centrifuged to separate the fraction I protein by collecting the 18 Svedberg unit peak; thereafter exchanging a low salt buffer for the sucrose, such as by dialysis against the low salt buffer; and finally precipitating the fraction I protein by adding a precipitant, such as $(NH_4)_2SO_4$ in an amount to achieve 30 to 50% precipitant saturation.

EXAMPLE I

The procedure described here is a modification of the method developed by Chan et al. for purification of tobacco fraction I protein.

Fresh leaves from 10 day-old corn, 4 to 6 week-old potato or tomato, 8 to 10 week-old tobacco or alfalfa, 6 to 8 week-old or market spinach, and 6 to 10 week-old cotton are harvested and kept on ice. The leaves are washed with ice water (distilled), quickly dried with paper towels, and weighed at room temperature (fresh weight). The leaves are then kept on ice or placed in cold storage until homogenization in Buffer A (Buffer A: 1.0 M NaCl, 2 mM $MgCl_2$, 1 mM $Na_2EDTA$ (sodium salt of ethylene diamine tetra-acetic acid) and 50 mM Tris-HCl, pH 7.8 at 4° C.; 0.1 M 2-mercaptoethanol was added just prior to use) (2.0 ml/gm fresh weight leaves) for 1 min. at 4° C. in a precooled Waring blendor. In some cases, where the leaf material is highly vascularized and difficult to homogenize (i.e., corn and alfalfa), leaves may be deribbed and the tissue diced prior to homogenization. Up to 8 ml of Buffer A per gram fresh weight leaf tissue is recommended. Corn leaves are best homogenized by hand with a mortar and pestle using glass beads or sand. The homogenate is squeezed through a layer of Miracloth and two layers of cheesecloth. The filtrate from all preparations, except tobacco and tomato, is centrifuged in a Sorvall centrifuge (SS-34 rotor) at 31,000 g (max) for one hour. Tobacco and tomato filtrates should be centrifuged at 105,000 g (max) for one hour for complete clarification.

The golden-colored supernatant solution (up to 600 ml) is passed through a G-25 Sephadex column (15×35 cm) at 22°–25° C. (room temperature) previously equilibrated with low salt Buffer B (Buffer B: 0.2 M NaCl, 0.5 mM $Na_2EDTA$, and 25 mM Tris-HCl, pH 7.4 at room temp.). Column size and sample volume may be altered proportionately. The column is eluted with Buffer B, and the eluant is continuously checked for the presence of precipitable protein using 10% trichloroacetic acid to determine when to start collecting the fraction I protein. The first 10% trichloroacetic acid-precipitable protein fraction is collected and the protein precipitated by addition of solid $(NH_4)_2SO_4$ to 30% (215.7 g/liter) saturation (4° C.). The precipitate is discarded, and the protein solution collected until brought to 50% (359.5 g/liter) saturation with $(NH_4)_2SO_4$. The precipitant is pelleted by centrifugation, resuspended in a minimum volume of Buffer B, and dialyzed* overnight against 50 volumes excess of Buffer B to remove $(NH_4)_2SO_4$.

*Dialyses disclosed herein are accomplished using cellulose dialysis tubing (1¼" width-⅜" diameter), boiled in 1 mM EDTA, 10 mM sodium bicarbonate and given several changes of distilled $H_2O$ prior to use.

EXAMPLE 1A

A modified form of Example 1 is recommended for purification of fraction I protein from cotton and any other plant species containing gossypol or other phenolic compounds. Freshly harvested, washed cotton leaves are homogenized with a precooled Waring Blendor in a high salt borate buffer (1.0 M NaCl, 2 mM $MgCl_2$, 1 mM $Na_2S_2O_5$, and 50 mM Na-borate buffer, 1 mM EDTA pH 7.6 at 4° C.) by blending 8.0 ml buffer/gm fresh weight leaves, and solid $(NH_4)_2SO_4$ is added to 30% saturation. After standing for 15 minutes at 4° C., the solution is filtered through a layer of Miracloth and two layers of cheesecloth. The filtrate is centrifuged at 14,600 g (max), for 30 min. and the supernatant fluid passed through a Sephadex G-25 column (22°-25° C.) equilibrated with a low salt borate buffer (0.2 M NaCl, 0.5 mM $Na_2EDTA$, 0.1 M $Na_2S_2O_5$, and 25 mM Na-borate buffer, pH 7.6 at 4° C.) The protein then is collected from the G-25 eluant as a 30% to 50% saturation $(NH_4)_2SO_4$ fraction and resuspended in and dialyzed against Buffer B. Ultimate purification is effected using an equivolumetric gradient of 5% to 35% (w/w) sucrose in Buffer B prepared in a Beckman Ti 14 zonal rotor. The sample (approximately 10 ml; 300–500 mg protein) is applied to the top of the gradient and centrifuged at 90,000 g (max) for 18 hours (4° C.). The homogeneous 18S fraction I protein peak is collected, dialyzed against 20 volumes excess of Buffer B for 6–12 hours at 4° C. to remove sucrose and precipitated by addition of $(NH_4)_2SO_4$ to 50% saturation. Sedimentation in other zonal rotors or swinging bucket rotors may be substituted for the Ti 14 zontal rotor. Any sucrose gradient with roughly equivalent parameters should provide similar fractionation.

Fraction I protein is purified readily in gram quantities from potato, tomato, tobacco, alfalfa and corn by the method described in Science, 204, pages 75–77 (1979), Johal, S. and Bourque, D. P. Fraction I protein from cotton also is purified readily if, as described, a borate buffer, i.e., 0.05 M is used during extraction. Presumably, the borate complexes with gossypol, an abundant phenolic compound in cotton leaves, and inhibits the effects of phenolic oxidation apparently occurring when the usual Tris-HCl buffer is employed for extraction. The borate buffer is recommended for other plant species in high polyphenols are abundant. Fraction I protein purified with or without the borate buffer yields crystals by the crystallization methods described herein. The precipitation by 30% saturation ammonium sulfate prior to centrifugal clarification of the crude homogenate also apparently aids the removal of gossypol and the stabilization of the fraction I protein from cotton. The zonal centrifuge-purified (18S) enzyme extracted from each of these species is about 95% pure and possesses both carboxylase and oxygenase activities. The entire purification (excluding crystallization) requires about 48 hours.

The presence of NaCl during homogenization is unnecessary for some species, for example, cotton and alfalfa. However, in the absence of an established purification protocol, the addition of NaCl at a concentration of at least 0.2 M is advisable. Its presence during purification has no apparent effect on the crystallization of fraction I protein or enzyme activity and may be required to prevent precipitation during the crystallization procedure, as in the case of potato and tobacco, to maintain fraction I protein integrity.

II. Crystallization

Crystallization of fraction I protein, as opposed to precipitation in amorphous form, is desirable, particularly to obtain a protein suitable for human ingestion as a nutritional supplement, since the crystals can be separated in substantially pure form, whereas a precipitate traps many impurities from solution. Crystallization of fraction I protein from plant leaves is accomplished in accordance with the present invention by a number of alternative methods.

In accordance with an important feature of the present invention, it has been found that a fraction I protein solution, when mixed with a precipitant solution having a pH generally within the range of 4.8–7.2 in an amount and at a pH sufficient to provide a mixed solution (protein solution mixed with precipitant solution) having a final pH in the range of 6.6–7.0, causes crystallization of fraction I protein from plant leaves provided that the precipitant solution is at a pH lower than the pH of the protein solution.

In accordance with the present invention, it has been found that a fraction I protein solution, when initially jolted with a precipitant solution having a lower pH, particularly when the precipitant solution has a pH at least 1.0 lower than the fraction I protein solution, will cause the protein to begin to nucleate while the lower pH precipitant solution is mixed with the protein solution to obtain a final (mixed solution) pH in the range of 6.6 to 7.0. This result is quite surprising since the final pH of the mixed solution may be very close to the initial pH of the protein solution and since the protein solution "sees" the low pH of the precipitant solution for a very short time before the pH is stabilized. More surprisingly, it has been found that by treating a fraction I protein solution in this manner, crystallization can be obtained from all fraction I protein species investigated.

To achieve the full advantage of the present invention, the precipitant solution should have a pH at least 1.0 lower than the pH of the protein solution. Optimum results have been obtained when the pH of the precipitant solution is in the range of 5.0 to 6.0. For certain species such as potato and tobacco, the protein solution should include a salt, such as sodium chloride, having the capability of increasing the solubility of the protein in water, to avoid the precipitation of fraction I protein in amorphous form before conditions are proper for crystallization.

In brief, crystallization of fraction I protein is accomplished, in accordance with the present invention, by (1) substitution of a potassium phosphate buffer for the sucrose (or other gradient) used in fraction I purification, such as by dialysis of the sucrose gradient-purified fraction I protein against a substantial excess, i.e., 100 volumes, of a potassium phosphate buffer; (2) optionally clarifying the protein solution such as by centrifugation; (3) diluting the supernatant protein solution with the potassium phosphate buffer to a concentration of 1 to 50 mg. protein/ml., preferably in the range of 5 to 15 mg. protein/ml., at a pH above 6.6 and generally in the range of 6.6 to 8.8 to ensure gradual dehydration to a condition of supersaturation; (4) mixing the protein solution with a precipitant solution, such as polyethylene glycol, having a pH in the range of 4.8 to 7.2, the precipitant solution having a lower pH than the pH of the protein solution and mixed with the protein solution in an amount and at a pH such that the mixed solution of protein and precipitant has a final pH in the range of 6.6 to 7.0; and (5) dehydrating the protein solution to achieve supersaturation and crystallization.

Dehydration of the protein solution can be accomplished in a number of ways, such as by vapor diffusion in a sealed container or by dialysis or the like, but in each case, dehydration should take place slowly to ensure crystallization, i.e., crystallization does not occur for at least 8 hours using a desiccant and sometimes a week or more using the equilibrium vapor diffusion dehydration method. To achieve the full advantage of the present invention, the precipitant solution should have a pH at least 1.0 lower than the pH of the protein solution. Optimum results have been obtained when the pH of the precipitant solution is in the range of 5.0 to 6.0 with a protein solution in the range of 7.0 to 7.5.

EXAMPLE 2

Method 1: Analytical vapor diffusion with polyethylene glycol 6000*: The sucrose gradient-purified fraction I protein from most plant species is dialyzed overnight against 100 volumes of Buffer C (Buffer C: 50 mM potassium phosphate, pH 7.2 at room temperature containing 3 mM NaN$_3$). The protein solution is clarified by centifugation (27,000 g (max); 15 min.) and diluted with Buffer C to 10 mg/ml. A 25-50 ul droplet of the protein is then mixed with an equal volume of 8% (w/v) solution of polyethylene glycol 6000 in Buffer D in a micro spot plate depression (Buffer D: 50 mM potassium phosphate, pH 5.4 at room temperature and 3 mM NaN$_3$). The final pH of this mixed solution is 6.7. The spot plates, supported on a platform, are placed in a photocube above a 150 ml reservoir (see drawing) of precipitant solution (8% (w/v) solution of polyethylene glycol 6000 in Buffer D) and left undisturbed for 2-3 weeks. The pH of the buffered polyethylene glycol 6000 solution (precipitant solution) can be varied, if necessary, from 4.8 to 7.2 (by adjusting with a suitable strong base, such as KOH) resulting in a mixed solution final pH, after mixing with protein solution, in the range of from 6.6 to 7.2.

*Flake form (Fisher Scientific Co., Fairlawn, N.J.).

EXAMPLE 3

Example 3 follows the procedure of Example 2 except that 10 mM NaCl is included in Buffer C. The NaCl has been found to be necessary for crystallization of fraction I protein from tobacco and potato. Other plant species which have not been specifically disclosed herein, may also require the presence of salt during crystallization.

EXAMPLE 4

Method 2: Analytical vapor diffusion with potassium phosphate-(NH$_4$)$_2$SO$_4$ solutions: Fraction I protein from tobacco (or potato) is diluted with Buffer D containing 10 mM NaCl to 10 mg/ml and clarified by centrifugation (27,000 g (max); 15 min.). Fraction I protein from tomato is diluted in Buffer C and the same procedure followed. The protein is mixed thoroughly in a spot plate depression with an equal volume of 0.375 M (NH$_4$)$_2$SO$_4$ (see the drawing) in Buffer D for 2-3 weeks. As in Examples 2 and 3, the pH of the potassium phosphate-(NH$_4$)$_2$SO$_4$ solution can be varied from pH 4.8 to 7.2 by adjustment with any base, such as KOH.

EXAMPLE 5

Method 3: Preparative crystallization by vapor diffusion with polyethylene glycol 6000*: Three ml each of 8% (w/v) solution of polyethylene glycol 6000 in Buffer D (or in water) and protein (10 mg/ml in Buffer C or in Buffer C plus 10 mM NaCl) were mixed in a petri dish. The dish is placed in a dessicator containing silica gel desiccant (as a replacement for the precipitant solution in the drawing) which was evacuated and sealed. Crystals form within 12-24 hours at 22°-25° C. (room temperature).

*Flake form (Fisher Scientific Co., Fairlawn, N.J.)

EXAMPLE 6

Method 4: Preparative crystallization of potato, tobacco, and tomato fraction I protein by dialysis against potassium phosphate-(NH$_4$)$_2$SO$_4$ mixtures: Tobacco (or potato) fraction I protein at 10 mg/ml in Buffer C containing 10 mM NaCl, or tomato enzyme in Buffer C, was dialyzed for 48 hours at 22°-25° C. (room temperature) against 100 volumes of Buffer D containing 0.375 M (NH$_4$)$_2$SO$_4$ adjusted to pH 5.4 to achieve crystallization.

Optimum conditions for fraction I protein crystal growth from specific plant species (also see Tables 1 and 2)

Spinach: Using Method 1 (Example 2) or Method 3 (Example 5) small crystals grow at 4° C. At 22°-25° C., Method 3 (protein in Buffer C) yields well formed crystals within 12-24 hours. The crystallization temperatures generally can be adjusted +/−10° C. while achieving acceptable crystallization. The optimum pH of the precipitant (polyethylene glycol) solution is 5.4 corresponding to a mixed solution at pH 6.7. Tetragonal bipyramids and other crystal habits ranging in size from 5 to 50 μm, are found after 2-3 weeks of growth.

Tobacco: (A) By the Method of Example 2, flat plate and rod-shaped crystals form at room temperature (22°-25° C.). Method 3 (Example 5) using Buffer C containing 10 mM NaCl yields large amounts of crystals within 12-24 hours at room temperature (22°-25° C.). (B) Using Method 2 (Example 4), large, well-formed crystals suitable for x-ray diffraction are obtained after 2 weeks at room temperature (22°-25° C.). Method 4 (Example 6) gives large amounts of crystals within 48 hours using 2 to 5 ml protein solution at 10 mg/ml.

Alfalfa: Rosette-shaped crystals are obtained by Method 1 (Example 2) at room temperature (22°-25° C.). The crystals reach 50-200 μm in length after 2-3 weeks and are the largest of the crystals grown by Method 1. The crystal plates often seem to emanate from a nuclear crystal of undetermined habit. The pH of the mixed solution from which alfalfa fraction I protein is crystallized is 6.65 to 7.2, corresponding to a pH of the precipitant solution of 4.8-7.2. Method 3 (Example 5) yields large quantities of crystals.

Cotton: Method 1 (Example 2) and Method 3 (Example 5 using protein in Buffer C) yields crystals under the same conditions and with the same morphologies as spinach. Conditions for crystallization of fraction I protein from cotton by Method 1 (Example 2) are identical to those of spinach (Table 1). The predominant habit of cotton fraction I crystals is also the tetragonal bipyramid and their size is comparable to that of the spinach crystals.

Potato: (A) Flat plate shaped crystals are obtained by Method 1 (Example 2) at 4° C. (B) Method 2 (Example 4 using protein in Buffer D containing 10 mM NaCl) yields large, well-formed crystals at room temperature (22°-25° C.) suitable for x-ray diffraction. Method 4 (Example 6 using protein in Buffer C containing 10 mM NaCl) gives crystals at 4° C., or room temperature (22°-25° C.) with the 0.375 M (NH$_4$)$_2$SO$_4$ precipitant solution at pH 4.8 to 5.8.

Tomato: (A) Method 1 (Example 2) yields flat rods with 8% (w/v) solution of polyethylene glycol 6000 pH 4.8-7.0, and plates with 4% (w/v) solution of polyethylene glycol 6000, pH 4.8-6.8, at room temperature (22°–25° C.). To date, this is the only species observed to exhibit precipitant concentration-dependent crystal morphology. (B) Method 2 (Example 4 using protein in Buffer C) yields stellate regular hexahedreon-shaped crystals at room temperature (22°–25° C.) with the precipitant solution at pH 4.8–7.0. Method 4 (Example 6 using protein in Buffer C) gives less well-shaped crystals at room temperature (22°–25° C.) after 2 days.

Corn: Method 1 (Example 2) with precipitant at pH 5.4–6.2 yields rosettes of flat plate crystals at 4° C. which are similar to the alfalfa crystals.

CONCLUSIONS AND OBSERVATIONS

Prior to the present invention, fraction I protein has been crystallized (as Form I) from many species of Nicotiana under identical, low salt dialysis conditions (Singh, S., and Wildman, S. G. (1973), Molec. Genet. 124, 187–196). I have found that fraction I protein, isolated from several taxonomically diverse species, crystallizes under similar conditions. More particularly, I have found two sets of solution conditions that have yielded macroscopic crystals of fraction I protein from seven different plants. The conditions of Method 1 (Examples 2-3) have produced crystals from seven species, and have not failed to produce crystals in any instance. My detailed results teach that it may be necessary to vary the parameters of crystallization somewhat from species to species. For example, 10 mM NaCl should be added to crystallize fraction I protein from potato or tobacco and the temperature should be lowered from room temperature (i.e., 4° C.) for crystallization of fraction I protein from corn, spinach, cotton, and potato. Crystallization occurred readily at room temperature +/10° C. from alfalfa, tomato and tobacco (see Table 1).

TABLE I

Crystallization of RuBisCo by Vapor Diffusion Using Polyethylene Glycol 6000 as Precipitant

| Species | Crystal habit | Temperature/ °C. | NaCl concentration | pH of precipitant |
|---|---|---|---|---|
| Alfalfa | Flat plate rosettes | 22–25 | — | 4.8–7.2 |
| Tomato | Flat plate | 22–25 | — | 4.8–6.8 |
|  | Rod | 22–25 | — | 4.8–7.0 |
| Corn | Flat plate | 4 | — | 5.4–6.2 |
| Spinach | Tetragonal bipyramid | 4 | — | 4.8–7.2 |
| Cotton | Tetragonal bipyramid | 4 | — | 4.8–7.2 |
| Potato | Flat plate | 4 | 10 mM | 6.2 |
| Tobacco | Flat plate | 22–25 | 10 mM | 5.4 |

The second set of conditions are those of Method 2 (Example 4), wherein ammonium sulfate replaces polyethylene glycol 6000 as the precipitant. These conditions also should be varied somewhat for optimum crystal growth, as set forth in Table 2.

TABLE 2

Crystallization of RuBisCo by Vapor Diffusion Using (NH$_4$)$_2$SO$_4$ as Precipitant

| Species | Crystal habit | Temperature/ °C. | NaCl concentration | pH of precipitant |
|---|---|---|---|---|
| Potato | Tetragonal | 22–25 | 10 mM | 4.8–6.2 |
| Tobacco | bipyramid Rhombid dodecahedron | 22–25 | 10 mM | 5.4 |
| Tomato | Stellate regular hexahedron | 22–25 | — | 4.8–7.0 |

Several different proteins previously have been crystallized by vapor diffusion using polyethylene glycol as a precipitent (McPherson, A. Jr. (1976) J. Biol. Chem. 251, 6300–6303), however, the capability of crystallizing fraction I protein, in accordance with the present invention under similar conditions from a variety of species is very atypical of proteins. For example, McPherson in his review of protein crystal growth (McPherson, A., Jr. (1976), Methods of Biochemical Analysis 23, 249–345) states, "There is often a wide variability in the ease and quality with which proteins and nucleic acids can be crystallized in going from species to species . . . . Presumably because the lattice forces rely on so few contacts between molecules, only very minor changes in surface charge or residue disposition may have a profound effect on the macromolecular interactions." The capability of crystallizing several fraction I proteins under similar conditions in accordance with the present invention suggests that the surface charges and residue disposition of the molecule have been conserved in fraction I protein to an unusual extent. Indeed, the isoelectric points of fraction I protein from tobacco, spinach, cotton, and corn are almost identical in the presence of the activators, MgCl$_2$ and NaHCO$_3$, or the substrate, ribulose-1,5-bisphosphate.

Crystals of fraction I protein grown by Method 2 (Example 4) and crystals of fraction I protein from two species of tobacco grown by related method 4 (Example 6) where examined by x-ray diffraction and it was found that all three crystals have the same packing of the form III crystal, grown by slow dialysis. This suggests that Form III crystals are nucleated by the initial jolt of the protein solution with a lower pH precipitant solution when the mixed solution is formed in accordance with the present invention, and that the nuclei grow into crystals either after the pH is raised (when the pH of the mixed solution stabilizes) as in Method 2 (Example 4) or if the mixed solution remains at a very low pH, for example in the range of 5.0 to 6.0 as in Method 4 (Example 6).

The crystals grown by Method 1 (Examples 2 and 3) are nucleated by a low pH precipitant solution nucleation step at about pH 5.4 but the precipitant is now 8% (w/v) polyethylene glycol 6000. Because of the low pH nucleation, we might suspect that these crystals are also Form III. In fact, the crystals from spinach and cotton appear virtually identical in their tetragonal bipyramidal habit to the crystals of potato, and crystals of *Nicotiana tabacum*, both known to be Form III. In contrast, the other crystals grown by Method 1 have a flat plate habit, more reminiscent of Form II crystals (line 2 of Table 3).

TABLE 3

Comparison of Crystallizing Conditions for RuBisCO Crystal Forms

| Crystal form | Morphology | Method | Protein solution | Precipitant |
|---|---|---|---|---|
| Form I | Rhombic dodecahedrans | Dialysis | 24 mM Tris, pH 7.4–8.8 20 mM NaCl | 24 mM Tris, pH 7.4–8.8 |
| Form II | Square plates Triangular prisms | Dialysis | 24 mM Tris, pH 7.4 | 50 mM K-phosphate, pH 6 |
| Form II | | Mixing with precipitant followed by vapor diffusion | 20 mM NaCl Tris buffer, pH 7.8, 70 mM NaCl | 4% PEG 6000 |
| Form III | Pseudo-rhombic dodecehedrans | Dialysis | 50 mM K-phosphate, pH 7.2 | 300 mM $(NH_4)_2SO_4$ 200 mM K-phosphate in pH 5.2 |
| Form III | Tetragonal bipyramids | Methods 2 and 4 | 50 mM K-phosphate, pH 7.2 (10 mM NaCl)* | 375 mM $(NH_4)_2SO_4$ in 50 mM $KH_2PO_4$, pH 5.4 |
| Unknown: possibly mixed | Varied* | Methods 1 and 1a | 50 mM K-phosphate, pH 7.2 (10 mM NaCl)* | 8% PEG in 50 mM $KH_2PO_5$, pH 5.4 |

*Depending on species, see Tables 1 and 2.

However, crystal habit is known to reflect rates of growth more than internal structure. In short, at least two of the four crystals grown by Method 2 are Form III, and the crystals grown by Method I (Examples 2 and 3) may be Form III, but there is no firm evidence.

The reason why fraction I protein can be crystallized, in accordance with the present invention, from taxonomically diverse plants under similar conditions is not yet known. The possibility mentioned above is that the disposition of some residues on the molecular surface is conserved throughout the various species. This leads in turn to the question of why the surface of fraction I protein should be conserved more strongly than those of other proteins, which do not usually crystallize from similar solutions. The answer must be that some surface residues are adapted to crucial function(s) which may be disrupted by any change. This function may be related to regulation of enzymatic activity or to the protein's propensity to crystallize in the Form III structure. Enzymatic activities were measured before and after crystallization as set forth in Table 4.

TABLE 4

Enzymic Activities of RuBisCO before and after Crystallization.

| Species | $N^a$ | Carboxylase Activity $\frac{\mu moles\ CO_2}{mg - protein - min}$ | $N^a$ | Oxygenase Activity $\frac{\mu moles\ O_2}{mg - protein - min}$ |
|---|---|---|---|---|
| Spinach[b] | | | | |
| Before | 11 | $0.85(\pm.07)^c$ | 8 | $0.08(\pm.01)^c$ |
| After | 11 | $0.94(\pm.09)$ | 8 | $0.08(\pm.02)$ |
| Tobacco[d] | | | | |
| Before | 6 | $0.19(\pm.02)$ | 5 | $0.02(\pm.01)$ |
| (1) Method 3 crystals | 6 | $0.19(\pm.02)$ | 5 | $0.02(\pm.01)$ |
| (2) Method 4 crystals | 6 | $0.16(\pm.02)$ | 5 | $0.02(\pm.01)$ |
| (3) Low-salt dialysis | 6 | $0.24(\pm.03)$ | 5 | $0.03(\pm.01)$ |
| Alfalfa[d] | | | | |
| Before | 6 | $0.17(\pm.03)$ | 8 | $0.04(\pm.01)$ |
| After | 6 | $0.18(\pm.02)$ | 8 | $0.04(\pm.02)$ |
| Cotton[e] | | | | |
| Before | 3 | $0.08(\pm.01)$ | 4 | $0.010(\pm.001)$ |
| After | 3 | $0.08(\pm.01)$ | 4 | $0.010(\pm.004)$ |
| Potato[d] | | | | |
| Before | 7 | $0.18(\pm.01)$ | 8 | $0.03(\pm.01)$ |
| After | 7 | $0.22(\pm.02)$ | 8 | $0.03(\pm.01)$ |
| Tomato[e] | | | | |
| Before | 3 | $0.08(\pm.01)$ | 4 | $0.020(\pm.004)$ |
| (1) Method 3 crystals | 3 | $0.09(\pm.01)$ | 4 | $0.020(\pm.003)$ |
| (2) Method 3 crystals | 3 | $0.08(\pm.01)$ | 4 | $0.020(\pm.001)$ |

[a]Number of measurements.
[b]Data from three different preparations.
[c]Uncertainties represent maximum deviation from the mean of the measurements.
[d]Data from two different preparations.
[e]Data from one preparation.

Factors Affecting Crystallization

Crystals grown by near-equilibrium vapor diffusion (Examples 2–5) usually reach full size within two weeks and are often as large as 50 to 500 $\mu$m. When attempting to crystallize fraction I protein from a new species, success is achieved most readily by using Method 1 (Examples 2 and 3—vapor diffusion with 8% (w/v) polyethylene glycol 6000) or Method 2 (Example 4—vapor diffusion with 0.375 M ammonium sulfate). Other polyethylene glycols of other molecular weight ranges (600, 1000, 4000, and 20,000) also were examined as possible precipitants, but such substitutions produced protein precipitate and microcrystals in most cases. One exception is that polyethylene glycol 4000 is effective for crystallization of fraction I protein from tomato.

The pH of the initial enzyme solutions (protein solution just prior to admixture with the precipitant solution) can be within the full range of 6.7 to 7.2, but if fraction I protein is stored in potassium phosphate buffers below pH 6.7 it cannot subsequently be crystallized. This emphasizes the importance and surprising nature of the pH of the precipitant solution in accordance with the present invention, since best results have been obtained by mixing the protein solution with a potassium phosphate buffered precipitant solution at a pH of 5.0 to 6.0. Upon mixing equal volumes of precipitant solution (at pH 5.4) and protein solution (at pH 7.2), a mixed solution of pH of 6.7 is obtained (see Examples 2–6). A mixed solution of pH 6.7 yielded the largest crystals. However, for most species, by altering the pH of the polyethylene glycol 6000, crystals could be grown from mixed solutions having values from pH 6.6 to 7.2. Fine adjustment of the pH is not necessary for crystallization of fraction I protein purified from species such as spinach and alfalfa, since crystallization is possible over the full range of mixed solution pH values from 4.8 to 7.2, or with unbuffered, 8% (w/v) polyethylene glycol 6000 as the precipitant.

The role of electrolytes, pH, temperature, ionic strength, cofactor(s) and possibly other parameters affecting the solubility properties of a protein are very important for successful crystallization of fraction I protein. In addition, a proper precipitant solution should be selected and the solubility behavior of the protein of interest determined in the presence of the precipitant. Once they have been established as disclosed herein, it is well within the skill of the art, following the disclosure herein, to systematically vary each important parameter in small increments in the presence of the precipitant to determine the effect on solubility.

From this information, a solubility minimum is identified for one or several parameters. At these minima, the most common observation is the precipitation of amorphorous or microcrystalline material. The critical point of supersaturation is approached slowly, since formation of large crystals depends on a very slow decrease in protein solubility. Other factors which can contribute to the effectiveness of crystallization are purity, protein concentration, and inhibition of proteases during purification. Once the conditions for crystallization have been established, larger crystals can often be grown by means of a slower approach to equilibrium or by readjusting certain parameters very slightly, (e.g., a small change in pH).

For fraction I protein, five parameters play an important role in crystallization:

(1) NaCl: For some species (e.g., tobacco and potato), 10 mM NaCl is used to prevent the enzymes from precipitating prematurely in the early stages of crystallization.

(2) pH: It has been discovered that enzymes stored below pH 6.7 precipitate out of solution and that crystal growth is enhanced if the enzyme is kept at pH 7.2. Precipitant pH also proved important in some instances (e.g., potato and corn fraction I protein) where crystallization is favored in a narrow range of final pH.

(3) Precipitant Solution: Polyethylene glycol 4000, 6000 and $(NH_4)_2SO_4$ are effective precipitants. Optimal results are obtained with $(NH_4)_2SO_4$ at a concentration of 0.375 M.

(4) Temperature: Some fraction I proteins (e.g., spinach, cotton, potato, and corn) crystallize at 4° C. whereas others crystallize at room temperature (22°–25° C.). Therefore, crystallization attempts for a new species should be carried out simultaneously at these two temperatures.

(5) Buffer: In general, the high salt Buffer A (Example 1) is useful for extraction of fraction I protein from a variety of plants and potassium phosphate (Examples 2–6) is extremely effective for use in crystallizing the enzyme from all sources tested. Fraction I protein from several other plants has been crystallized using this buffer. For plants such as cotton, whose leaves contain large amounts of polyphenols, a borate buffer (Example 1A) should be used for the initial purification steps. Other buffers are known to be satisfactory for purification of the enzyme prior to crystallization.

Crystalline fraction I protein from each of the species examined is at least 95% pure and the carboxylase and oxygenase activites before and after crystallization are comparable (see Table 4). In the case of spinach and alfalfa the crystalline fraction I protein can be stored for at least several weeks without affecting carboxylase activity. This is probably also true for the other crystalline fraction I proteins. Before assaying carboxylase and oxygenase activities for crystals grown with potassium phosphate-$(NH_4)_2SO_4$ solutions, the $(NH_4)_2SO_4$ should be removed by dialysis or gel filtration. Ammonium sulfate is a competitive inhibitor of fraction I protein. The presence of 1–2% (w/v) polyethylene glycol 6000 in the carboxylase reaction mixture reduces the activity to 80–90% of that obtained in the absence of polyethylene glycol. The enzyme can be freed of polyethylene glycol, for example, by DEAE ion exchange chromatography.

I claim:

1. A method of crystallizing fraction I protein from a photosynthetic organism comprising:
   separating and purifying protein from said photosynthetic organism;
   mixing said protein in a suitable solvent to form a protein solution at a predetermined pH;
   mixing a precipitant solution with said protein solution, said precipitant solution having a pH lower than the pH of the protein solution and within the range of 4.8 to 7.2 to form a mixed solution having a pH in the range of 6.6 to 7.0; and
   removing a portion of said solvent from said mixed solution to cause said protein to crystallize.

2. A method as defined by claim 1 wherein said protein solution has a pH of 7.0 to 7.5 and said precipitant solution has a pH of 4.8 to 6.0.

3. A method as defined by claim 1 wherein said protein solution has a pH of 7.0 to 7.5 and said precipitant solution has a pH of 5.0 to 6.0.

4. A method as defined by claim 1 wherein said precipitant is selected from the group consisting of polyethylene glycol and ammonium sulfate.

5. A method as defined in claim 1 wherein said precipitant solution includes a potassium phosphate buffer and said precipitant solution has a pH in the range of 5.0 to 6.0.

6. A method as defined in claim 1 wherein said protein solution comprises fraction I protein dissolved in water buffered to a pH in the range of 6.8 to 8.8.

7. A method as defined in claim 6 wherein said protein solution contains an inert salt capable of increasing the solubility of protein in water.

8. A method as defined in claim 7 wherein said salt is NaCl at a protein solution concentration of 1.0 Molar, or less.

9. A method as defined in claim 1, wherein solvent removal from said mixed solution is accomplished by differential vapor diffusion in a sealed container.

10. A method as defined in claim 1 wherein said solvent is water and said solvent is removed from the mixed solution by disposing said mixed solution in a sealed container containing a desiccant.

11. A method as defined in claim 10 wherein said desiccant is silica gel.

12. A method as defined in claim 1 wherein said precipitant solution has a pH at least 1.0 lower than the predetermined pH of said protein solution.

13. A method as defined in claim 12 wherein said protein solution has a pH of 7.0 to 7.5, said precipitant solution has a pH of 5.0 to 6.0 and said mixed solution has a pH of 6.5 to 7.0.

14. A method of crystallizing fraction I protein from photosynthetic plant leaves comprising:
   homogenizing photosynthetic plant leaves in a buffer and water to obtain a homogenate comprising a liquid containing dissolved fraction I protein and solids;
   separating the liquid, containing dissolved fraction I protein, from the solids;
   precipitating the fraction I protein from the liquid with a fraction I protein precipitant;
   removing the precipitate from the fraction I protein precipitate;
   dissolving the precipitate in a suitable buffer at a predetermined pH to form a protein solution;
   adding a solution containing a fraction I protein precipitant to said protein solution, said solution containing said precipitant having a pH lower than the pH of the protein solution and in the range of 4.8 to 7.2, to form a mixed solution having a pH in the range of 6.6 to 7.0; and
   dehydrating said mixed solution to cause crystallization of fraction I protein.

15. A method as defined in claim 14 wherein said buffer used in homogenizing said plant leaves includes a salt capable of increasing the water solubility of fraction I protein, said salt being present at a concentration of at least 0.5 Molar.

16. A method as defined in claim 15 wherein said salt comprises NaCl.

17. A method as defined in claim 14 wherein said buffer used in homogenizing said plant leaves is combined with said plant leaves in an amount of 3-10 ml. buffer/gm. plant leaves based on the fresh weight of said plant leaves.

18. A method as defined in claim 15 further including the step, after homogenization, of exchanging a low salt buffer having a salt concentration of 0.3 Molar or less for said buffer used in homogenizing, said low salt buffer having a pH in the range of 6.8 to 8.8.

19. A method as defined in claim 18 wherein said low salt buffer is exchanged by dialysis.

20. A method as defined in claim 18 wherein the salt contained in said low salt buffer is NaCl.

21. A method as defined in claim 14 wherein said precipitant mixed with said protein solution to form a mixed solution is a water absorbant.

22. A method as defined in claim 14 wherein said precipitant mixed with said protein solution to form a mixed solution is selected from the group consisting of polyethylene glycol 4000, polyethylene glycol 6000 and ammonium sulfate.

23. A method as defined in claim 14 wherein said protein solution has a pH of 7.0 to 7.5 and said precipitant solution has a pH of 4.8 to 6.0.

24. A method as defined in claim 14 wherein dehydration of said mixed solution is accomplished by disposing said mixed solution in a sealed container containing a desiccant.

25. A method as defined in claim 14 wherein said precipitant solution has a pH at least 1.0 lower than the predetermined pH of said protein solution.

26. A method as defined in claim 25 wherein said protein solution has a pH of 7.0 to 7.5, said precipitant solution has a pH of 5.0 to 6.0 and said mixed solution has a pH of 4.8 to 7.2

27. A method as defined in claim 14 wherein said precipitant solution includes a potassium phosphate buffer and said precipitant solution has a pH in the range of 5.0 to 6.0.

28. A method as defined in claim 14 wherein said protein solution is buffered to a pH in the range of 6.8 to 8.8.

29. A method as defined in claim 14 wherein said protein solution contains a salt inert to said protein, and capable of increasing the solubility of said protein in water.

30. A method as defined in claim 29 wherein said salt is NaCl at a protein solution concentration of 1.0 Molar, or less.

31. A method as defined in claim 34 wherein said photosynthetic plant leaves comprise a mixture of two or more different plant leaf species.

32. A method as defined in claim 14 wherein said plant leaves are selected from the group consisting of alfalfa, corn, cotton, potato, spinach tomato, tobacco *Nicotiana sylvestris,* and tobacco *Nicotiana tabacum.*

33. A method as defined in claim 14 wherein said plant leaves are selected from the group consisting of alfalfa, corn, cotton and potato.

34. A method as defined in claim 14 further including the step of diluting the protein solution with a potassium phosphate buffer to a protein concentration of 1 to 50 mg. protein/ml., based on the dry weight of said protein, prior to dehydration.

35. A method as defined in claim 34 wherein said protein solution is diluted to a contration of 5-15 mg protein/ml.

36. A method as defined in claim 35 wherein said protein solution is diluted to a concentration of 10 mg protein/ml., based on the dry weight of said protein, prior to dehydration.

37. A method as defined in claim 30 wherein said salt concentration is 0.001 Molar to 0.2 Molar.

38. A method as defined in claim 37 wherein said buffer used in homogenization includes Tris-NCl at a concentration of at least 0.01 M.

39. A method of crystallizing fraction I protein from plant leaves comprising:
   homogenizing plant leaves in a buffer containing a salt in a concentration above 0.3 Molar, said salt capable of increasing the solubility of fraction I protein in water, at a pH of 7.0 to 8.8 to obtain a homogenate;

filtering the homogenate to separate solids from the homogenate while retaining the dissolved protein in the filtrate;

reducing the salt concentration in said filtrate to a value lower than 0.3 Molar;

diluting the filtrate with a potassium phosphate buffer to a pH of 6.7 to 7.2, to a concentration of 5 to 15 mg. protein/ml., to form a protein solution;

mixing a precipitant solution into said protein solution, said precipitant solution having a lower pH than the pH of the protein solution and said precipitant solution having a pH of 6.6 to 7.2, to form a mixed solution having a pH of 6.7 to 7.0; and dehydrating said mixed solution to cause crystallization of said fraction I protein.

40. A method as defined in claim 39 wherein said buffer used in homogenization of said plant leaves is a borate buffer and said salt concentration is 0.2 Molar, or less.

41. A method as defined in claim 40 wherein said plant leaves include cotton plant leaves.

42. A method as defined in claim 39 wherein said filtrate is further purified by passing said filtrate through a 5% to 35% sucrose gradient and the fraction I protein-containing filtrate collected from said gradient, and a substantial portion of any sucrose absorbed by said filtrate in said gradient removed prior to forming said mixed solution.

43. A method as defined in claim 42 further including precipitating said fraction I protein by addition of ammonium sulfate to 30% to 50% saturation, prior to forming a mixed solution.

44. A method as defined in claim 39 wherein said precipitant solution includes a potassium phosphate buffer.

45. A method as defined in claim 39 wherein the mixed solution has a pH of 6.7.

46. A method as defined in claim 39 wherein said protein solution contains NaCl in a concentration of 0.2 Molar or less.

47. A method as defined in claim 39 wherein said mixed solution is dehydrated by absorption of water by a desiccant.

48. A method as defined in claim 39 wherein said mixed solution is dehydrated by vapor diffusion with a solution of potassium phosphate and ammonium sulfate disposed in a substantially sealed container with said mixed solution.

49. A method of manufacture of a solution containing fraction I protein in a manner such that said protein solution is at conditions correct for crystallization of fraction I protein therefrom comprising:

separating and purifying protein from a photosynthetic organism;

mixing said protein in a suitable solvent to form a protein solution at a predetermined pH; and mixing a precipitant solution with said protein solution, said precipitant solution having a pH lower than the pH of the protein solution and within the range of 4.8 to 7.2 to form a mixed solution having a pH in the range of 6.6 to 7.0, said mixed solution being at conditions correct for crystallization.

50. A method as defined by claim 49 wherein said protein solution has a pH of 7.0 to 7.5 and said precipitant solution has a pH of 4.8 to 6.0.

51. A method of manufacture of a solution containing fraction I protein in a manner such that such protein solution is at conditions correct for crystallization of fraction I protein therefrom comprising:

homogenizing photosynthetic plant leaves in a buffer and water to obtain a homogenate comprising a liquid containing dissolved fraction I protein and solids;

separating the liquid, containing dissolved fraction I protein, from the solids;

precipitating the fraction I protein from the liquid with a fraction I protein precipitant;

removing the precipitant from the fraction I protein precipitate;

dissolving the precipitate in a suitable buffer at a predetermined pH to form a protein solution; and adding a solution containing a fraction I protein precipitant to said protein solution, said solution containing said precipitant having a pH lower than the pH of the protein solution and in the range of 4.8 to 7.2, to form a mixed solution having a pH in the range of 6.6 to 7.0, said mixed solution being at conditions correct for crystallization.

52. A method as defined by claim 51 wherein said protein solution has a pH of 7.0 to 7.5 and said precipitant solution has a pH of 4.8 to 6.0.

53. A method of manufacture of a solution containing fraction I protein in a manner such that said protein solution is at conditions correct for crystallization of fraction I protein therefrom comprising:

homogenizing plant leaves in a buffer containing a salt in a concentration above 0.3 Molar, said salt capable of increasing the solubility of fraction I protein in water, at a pH of 7.0 to 8.8 to obtain a homogenate;

filtering the homogenate to separate solids from the homogenate while retaining the dissolved protein in the filtrate;

reducing the salt concentration in said filtrate to a value lower than 0.3 Molar;

diluting the filtrate with a potassium phosphate buffer to a pH of 6.7 to 7.2, to a concentration of 5 to 15 mg. protein/ml., to form a protein solution; and mixing a precipitant solution with said protein solution, said precipitant solution having a lower pH than the pH of the protein solution and said precipitant solution having a pH of 6.6 to 7.2, to form a mixed solution having a pH of 6.7 to 7.0, said mixed solution being at conditions correct for crystallization.

54. A method as defined by claim 53 wherein said protein solution has a pH of 7.0 to 7.5 and said precipitant solution has a pH of 4.8 to 6.0.

55. A method of crystallizing fraction I protein from a photosynthetic organism comprising:

separating and purifying protein from said photosynthetic organism;

mixing said protein in a suitable solvent to form a protein solution at a predetermined pH;

mixing a precipitant solution with said protein solution, said precipitant solution having a pH lower than the pH of the protein solution and within the range of 4.8 to 7.2 to form a mixed solution having a pH in the range of 6.6 to 7.0; and supersaturating said mixed solution to cause said protein to crystallize.

56. A method as defined in claim 55 wherein said protein solution has a pH of 7.0 to 7.5 and said precipitant solution has a pH of 4.8 to 6.0.

57. A method of crystallizing fraction I protein from photosynthetic plant leaves comprising:
- homogenizing photosynthetic plant leaves in a buffer and water to obtain a homogenate comprising a liquid containing dissolved fraction I protein and solids;
- separating the liquid, containing dissolved fraction I protein, from the solids;
- precipitating the fraction I protein from the liquid with a fraction I protein precipitant;
- removing the precipitant from the fraction I protein precipitate;
- dissolving the precipitate in a suitable buffer at a predetermined pH to form a protein solution;
- contacting said protein solution with a solution containing a fraction I protein precipitant, said solution containing said precipitant having a pH lower than the pH of the protein solution and in the range of 4.8 to 7.2, to form a mixed solution having a pH in the range of 6.6 to 7.0; and
- supersaturating said mixed solution to cause crystallization of fraction I protein.

58. A method as defined in claim 57 wherein said protein solution has a pH of 7.0 to 7.5 and said precipitant solution has a pH of 4.8 to 6.0.

59. A method of crystallizing fraction I protein from a photosyntheic organism comprising:
- homogenizing plant leaves in a buffer containing a salt in a concentration above 0.3 Molar, said salt capable of increasing the solubility of fraction I protein in water, at a pH of 7.0 to 8.8 to obtain a homogenate;
- filtering the homogenate to separate solids from the homogenate while retaining the dissolved protein in the filtrate;
- reducing the salt concentration in said filtrate to a value lower than 0.3 Molar;
- diluting the filtrate with a potassium phosphate buffer to a pH of 6.7 to 7.2, to a concentration of 5 to 15 mg. protein/ml., to form a protein solution;
- mixing a precipitant solution with said protein solution, said precipitant solution having a lower pH than the pH of the protein solution and said precipitant solution having a pH of 6.6 to 7.2, to form a mixed solution having a pH of 6.7 to 7.0; and
- supersaturating said mixed solution to cause said protein to crystallize.

60. A method as defined in claim 59 wherein said protein solution has a pH of 7.0 to 7.5 and said precipitant solution has a pH of 4.8 to 6.0.

* * * * *

UNITED STATES PATENT AND TRADEMARK OFFICE
CERTIFICATE OF CORRECTION

PATENT NO. : 4,340,676
DATED : July 20, 1982
INVENTOR(S) : Don P. Bourque

It is certified that error appears in the above-identified patent and that said Letters Patent are hereby corrected as shown below:

Col. 16, line 37, "34" should be --14--;

Col. 18, line 2, "such" second occurrence should be --said--.

Signed and Sealed this

Fourteenth Day of December 1982

[SEAL]

Attest:

GERALD J. MOSSINGHOFF

Attesting Officer     Commissioner of Patents and Trademarks